(12) United States Patent  (10) Patent No.: US 9,533,108 B2
Salto et al.  (45) Date of Patent: Jan. 3, 2017

(54) SAFETY SHIELD FOR MEDICAL NEEDLES

(71) Applicant: Covidien LP, Mansfield, MA (US)

(72) Inventors: David J. Salto, Hopedale, MA (US); Eugene E. Weilbacher, Chesterfield, MO (US)

(73) Assignee: Covidien LP, Mansfield, MA (US)

( * ) Notice: Subject to any disclaimer, the term of this patent is extended or adjusted under 35 U.S.C. 154(b) by 486 days.

(21) Appl. No.: 14/013,050

(22) Filed: Aug. 29, 2013

(65) Prior Publication Data

US 2014/0074040 A1 Mar. 13, 2014

Related U.S. Application Data

(62) Division of application No. 11/452,643, filed on Jun. 14, 2006, now Pat. No. 8,551,051.

(60) Provisional application No. 60/692,324, filed on Jun. 20, 2005.

(51) Int. Cl.
*A61M 5/32* (2006.01)
(52) U.S. Cl.
CPC ......... *A61M 5/3243* (2013.01); *A61M 5/3271* (2013.01); *A61M 2005/3247* (2013.01); *A61M 2005/3252* (2013.01)
(58) Field of Classification Search
CPC ................... A61M 2005/3247; A61M 5/3202; A61M 5/3271; A61M 2005/3261; A61M 25/0631; A61M 5/3272; A61M 5/3243; A61M 2005/3252
See application file for complete search history.

(56) References Cited

U.S. PATENT DOCUMENTS

| | | |
|---|---|---|
| 2,559,474 A | 7/1951 | Son |
| 2,739,591 A | 3/1956 | Yochem |
| 4,160,450 A | 7/1979 | Doherty |
| 4,194,505 A | 3/1980 | Schmitz |
| 4,573,976 A | 3/1986 | Sampson et al. |
| 4,664,654 A | 5/1987 | Strauss |
| 4,725,267 A | 2/1988 | Vaillancourt |
| 4,738,663 A | 4/1988 | Bogan |
| 4,747,831 A | 5/1988 | Kulli |
| 4,762,516 A | 8/1988 | Luther et al. |
| 4,795,432 A | 1/1989 | Karczmer |

(Continued)

FOREIGN PATENT DOCUMENTS

| | | |
|---|---|---|
| CA | 2261938 C | 7/2004 |
| EP | 0680767 A1 | 11/1995 |

(Continued)

OTHER PUBLICATIONS

Non-Final Office action for U.S. Appl. No. 12/237,722 dated Sep. 22, 2014, 8 pages, Alexandria, Virginia, United States.

(Continued)

*Primary Examiner* — Emily Schmidt

(57) ABSTRACT

Medical needle shield apparatus for covering a needle after use. The medical needle shield apparatus includes a first member, such as, for example, a syringe barrel having a needle mounted therewith. A second member, such as, for example, a shield is mounted with the first member. The shield is movable between a first position whereby the needle is exposed and a second position whereby the needle is covered. A lock is mounted with the barrel such that the shield is slidably movable along an outer surface of the lock. The lock includes a tang that is movable radially outward to fix the shield in the second position.

17 Claims, 18 Drawing Sheets

(56) References Cited

U.S. PATENT DOCUMENTS

| | | |
|---|---|---|
| 4,900,307 A | 2/1990 | Kulli |
| 4,909,793 A | 3/1990 | Vining et al. |
| 4,911,693 A | 3/1990 | Paris |
| 4,947,863 A | 8/1990 | Haber et al. |
| 4,955,866 A | 9/1990 | Corey |
| 4,978,344 A | 12/1990 | Dombrowski et al. |
| 4,986,811 A | 1/1991 | Thead et al. |
| 4,994,041 A | 2/1991 | Dombrowski et al. |
| 4,994,046 A | 2/1991 | Wesson et al. |
| 5,026,356 A | 6/1991 | Smith |
| 5,045,066 A | 9/1991 | Scheuble et al. |
| 5,086,922 A | 2/1992 | Sagstetter et al. |
| 5,215,534 A | 6/1993 | De Harde et al. |
| 5,300,030 A | 4/1994 | Crossman et al. |
| 5,312,347 A | 5/1994 | Osborne et al. |
| 5,318,547 A | 6/1994 | Altschuler |
| 5,338,311 A | 8/1994 | Mahurkar |
| 5,338,331 A | 8/1994 | Hijikata et al. |
| 5,348,544 A | 9/1994 | Sweeney et al. |
| 5,423,766 A | 6/1995 | Di Cesare |
| 5,466,223 A | 11/1995 | Bressler et al. |
| 5,496,274 A | 3/1996 | Graves et al. |
| 5,501,675 A | 3/1996 | Erskine |
| 5,514,100 A | 5/1996 | Mahurkar |
| 5,527,287 A | 6/1996 | Miskinyar |
| 5,584,810 A | 12/1996 | Brimhall |
| 5,584,818 A | 12/1996 | Morrison |
| 5,599,310 A | 2/1997 | Bogert |
| 5,616,135 A | 4/1997 | Thorne et al. |
| 5,672,161 A | 9/1997 | Allen et al. |
| 5,685,862 A | 11/1997 | Mahurkar |
| 5,690,619 A | 11/1997 | Erskine |
| 5,702,369 A | 12/1997 | Mercereau |
| 5,738,665 A | 4/1998 | Caizza et al. |
| 5,865,806 A | 2/1999 | Howell |
| 5,879,337 A | 3/1999 | Kuracina et al. |
| 5,879,338 A | 3/1999 | Mahurkar |
| 5,891,105 A | 4/1999 | Mahurkar |
| 5,893,845 A | 4/1999 | Newby et al. |
| 5,910,130 A | 6/1999 | Caizza et al. |
| 5,911,705 A | 6/1999 | Howell |
| 5,957,887 A | 9/1999 | Osterlind et al. |
| 5,976,111 A | 11/1999 | Hart |
| 6,001,080 A | 12/1999 | Kuracina et al. |
| 6,086,562 A | 7/2000 | Jacobsen et al. |
| 6,117,112 A | 9/2000 | Mahurkar |
| 6,132,401 A | 10/2000 | Van Der Meyden et al. |
| 6,183,445 B1 | 2/2001 | Lund et al. |
| 6,193,696 B1 | 2/2001 | Jansen et al. |
| 6,280,401 B1 | 8/2001 | Mahurkar |
| 6,322,537 B1 | 11/2001 | Chang |
| 6,409,701 B1 | 6/2002 | Cohn et al. |
| 6,569,123 B2 | 5/2003 | Alchas et al. |
| 6,582,402 B1 | 6/2003 | Erskine |
| 6,638,254 B2 | 10/2003 | Nakagami |
| 6,761,706 B2 | 7/2004 | Vaillancourt |
| 6,767,336 B1 | 7/2004 | Kaplan |
| 7,407,493 B2 | 8/2008 | Cane' |
| 7,540,858 B2 | 6/2009 | DiBiasi |
| 7,670,314 B2 | 3/2010 | Wall et al. |
| 2002/0099338 A1 | 7/2002 | Young |
| 2002/0133122 A1 | 9/2002 | Giambattista et al. |
| 2003/0050607 A1 | 3/2003 | Gagnieux et al. |
| 2003/0149403 A1 | 8/2003 | Barker et al. |
| 2003/0187395 A1 | 10/2003 | Gabel et al. |
| 2004/0116847 A1 | 6/2004 | Wall |
| 2004/0116853 A1 | 6/2004 | Halseth et al. |
| 2005/0033230 A1 | 2/2005 | Alchas et al. |
| 2005/0038392 A1 | 2/2005 | DeSalvo |
| 2005/0080378 A1 | 4/2005 | Cindrich et al. |
| 2005/0113753 A1 | 5/2005 | Alchas et al. |

FOREIGN PATENT DOCUMENTS

| | | |
|---|---|---|
| EP | 0734738 A2 | 10/1996 |
| EP | 1568392 A1 | 8/2005 |
| WO | 9528979 A1 | 11/1995 |
| WO | 0145776 A1 | 6/2001 |
| WO | 0245786 A2 | 6/2002 |
| WO | 02083213 A1 | 10/2002 |
| WO | 2005016419 A1 | 2/2005 |
| WO | 2005053774 A1 | 6/2005 |

OTHER PUBLICATIONS

Non-Final Office action for U.S. Appl. No. 12/237,722 dated Nov. 14, 2014, 8 pages, Alexandria, Virginia, United States.

Non-Final Office action for U.S. Appl. No. 12/237,722 dated Oct. 22, 2015, 10 pages, Alexandria, Virginia, United States.

Non-Final Office action for U.S. Appl. No. 12/237,722 dated Apr. 23, 2014, 19 pages, Alexandria, Virginia, United States.

Extended European Search Report dated Oct. 17, 2006 in related European Patent Application No. 06253097.7, 4 pages.

Extended European Search Report dated Apr. 6, 2010 in related European Patent Application No. 08166654.7, 7 pages.

Response dated Nov. 2, 2010 to Extended European Search Report dated Apr. 6, 2010 in related European Patent Application No. 08166654.7, 12 pages.

Office Action dated Jan. 28, 2010 in related U.S. Appl. No. 12/237,722, 10 pages.

Response dated Apr. 28, 2010 to Office Action dated Jan. 28, 2010 in related U.S. Appl. No. 12/237,722, 10 pages.

Office Action dated Jul. 14, 2010 in related U.S. Appl. No. 12/237,722, 7 pages.

Response dated Oct. 12, 2010 to Office Action dated Jul. 14, 2010 in related U.S. Appl. No. 12/237,722, 10 pages.

Examiner's Report dated Jan. 27, 2011 in related Australian Application No. 2006202547, 1 page.

Response dated Oct. 11, 2011 to Examiner's Report dated Jan. 27, 2011 in related Australian Application No. 2006202547, 1 page.

Examiner's Report dated Jun. 17, 2013 in related Australian Application No. 2009222435, 3 pages.

Response dated Sep. 19, 2013 to Examiner's Report dated Jun. 17, 2013 in related Australian Application No. 2009222435, 8 pages.

Examiner's Report dated Nov. 1, 2013 in related Australian Application No. AU 2009222435, 3 pages.

Response dated Feb. 4, 2014 to Examiner's Report dated Nov. 1, 2013 in related Australian Application No. AU 2009222435, 6 pages.

Examiner's Report dated Jul. 11, 2012 in related Canadian Application No. 2550114, 2 pages.

Response dated Jan. 10, 2013 to Examiner's Report dated Jul. 11, 2012 in related Canadian Application No. 2550114, 3 pages.

Office Action dated Feb. 12, 2008 in related U.S. Appl. No. 11/452,643, 13 pages.

Response dated Apr. 23, 2008 to Office Action dated Feb. 12, 2008 in related U.S. Appl. No. 11/452,643, 8 pages.

Office Action dated Jun. 20, 2008 in related U.S. Appl. No. 11/452,643, 11 pages.

Response dated Nov. 17, 2008 to Office Action dated Jun. 20, 2008 in related U.S. Appl. No. 11/452,643, 19 pages.

Office Action dated Jan. 23, 2009 in related U.S. Appl. No. 11/452,643, 15 pages.

Response dated May 21, 2009 to Office Action dated Jan. 23, 2009 in related U.S. Appl. No. 11/452,643, 25 pages.

Office Action dated Jul. 30, 2009 in related U.S. Appl. No. 11/452,643, 13 pages.

Response dated Dec. 10, 2009 to Office Action dated Jul. 30, 2009 in related U.S. Appl. No. 11/452,643, 21 pages.

Office Action dated Feb. 23, 2010 in related U.S. Appl. No. 11/452,643, 15 pages.

Response dated Apr. 23, 2010 to Office Action dated Feb. 23, 2010 in related U.S. Appl. No. 11/452,643, 22 pages.

Advisory Action dated May 5, 2010 in related U.S. Appl. No. 11/452,643, 3 pages.

(56) References Cited

OTHER PUBLICATIONS

Appeal Brief dated Jul. 22, 2010 in related U.S. Appl. No. 11/452,643, 33 pages.
Examiners Answer dated Oct. 7, 2010 in related U.S. Appl. No. 11/452,643, 17 pages.
Reply Brief dated Dec. 7, 2010 in related U.S. Appl. No. 11/452,643, 16 pages.
Patent Board Decision dated Mar. 20, 2013 in related U.S. Appl. No. 11/452,643, 8 pages.
Notice of Opposition dated Jan. 27, 2011 in related European Patent Application No. 06253097.7, 33 pages.
Response dated Sep. 30, 2011 to Notice of Opposition dated Jan. 27, 2011 in related European Patent Application No. 06253097.7, 10 pages.
Extended European Search Report dated Jan. 29, 2010 in related European Patent Application No. 09170852.8, 3 pages.
Response dated Nov. 25, 2010 to Extended European Search Report dated Jan. 29, 2010 in related European Patent Application No. 09170852.8, 25 pages.
Office Action dated Jul. 13, 2011 in related Japanese Patent Application No. 2006-165823, 2 pages.
Non-Final Office action for U.S. Appl. No. 12/237,722 dated Feb. 4, 2015, 11 pages, Alexandria, Virginia, United States.

200~# SAFETY SHIELD FOR MEDICAL NEEDLES

CROSS-REFERENCE TO RELATED APPLICATIONS

The present application is a divisional of U.S. patent application Ser. No. 11/452,643 filed Jun. 14, 2006, which claimed priority to U.S. Provisional Patent Application Ser. No. 60/692,324 filed Jun. 20, 2005, the entire contents of which are incorporated by reference in their respective entireties.

BACKGROUND

1. Technical Field

The present disclosure generally relates to safety shields for medical needles, and more particularly, to manually activated safety shields that employ structure for positioning and locking a shield.

2. Description of the Related Art

Problems associated with inadvertent needle sticks are well known in the art of blood sampling, percutaneous medication injection, and other medical procedures involving use of medical needles. Significant attention has been focused on needle stick problems due to the contemporary sensitivity of exposure to AIDS, hepatitis, and other serious blood-borne pathogens.

Procedures for removing a needle from a patient commonly require a clinician to use one hand to place pressure at the wound site where a needle is being withdrawn, while removing the needle device with the other hand. It is also common practice for a clinician to give higher priority to care for the wound than is given to disposal of the needle. In the case of typical needle devices without safety shields, such priority either requires the convenience of an available sharps container within reach or another means for safe disposal, without leaving the patient's side. Thus, the difficulty in providing adequate care while following safety procedures is often compounded by the patient's physical condition and mental state, such as in burn units and psychiatric wards. Under such conditions, proper disposal of a used needle, while caring for a patient, is a technological challenge to the state of the art.

The widespread knowledge and history associated with needle care and disposal problems have resulted in numerous devices for minimizing accidental needle sticks. Some devices utilize a separate sheath or cap mounted over the needle after use. These devices, however, require two-handed manipulation from a practitioner.

Other known devices employ sheaths that are spring activated or pivoting. These devices, however, may disadvantageously misfire, be inadvertently activated, or cumbersome to activate. Further drawbacks of current devices include high manufacturing cost due to complexity and the number of parts. Thus, these types of prior art devices may not adequately and reliably shield needle infusion and/or fluid collection apparatuses to minimize hazardous exposure.

Consequently, there remains a need to provide a more satisfactory solution for needle safety devices by overcoming the disadvantages and drawbacks of the prior art. Therefore, it would be desirable to provide a more adequate and reliable safety apparatus having a medical needle shield that employs structure for positioning and locking a shield to minimize hazardous exposure to a needle. It would be desirable if the medical needle shield was actuated via one-handed operation. It would be highly desirable if the medical needle shield is easily and efficiently assembled and manufactured.

SUMMARY

In one particular embodiment, a safety apparatus is provided in accordance with the principles of the present disclosure. The safety apparatus includes a first member having a needle mounted therewith. A second member is mounted with the first member. A shield is movable between a first position whereby the needle is exposed and a second position whereby the needle is covered. A lock is mounted with the first member such that the second member is slidably movable along an outer surface of the lock. The lock includes a tang that is movable radially outward to fix the shield in the second position.

In an alternative embodiment, the safety apparatus includes a barrel. The barrel has a distal portion that defines a cavity. A needle extends from the cavity and has a distal end. A tubular shield is mounted within the cavity and is slidably movable relative thereto between a retracted position whereby the distal end of the needle is exposed and an extended position whereby the distal end of the needle is covered. A tubular lock insert is mounted with the distal portion of the barrel such that the shield is slidably movable along an outer surface of the insert. The lock includes a tang that is in substantial alignment with the outer surface of the insert during slidable movement of the shield. The tang is biased radially outward to fix the shield in the extended position.

In an alternative embodiment, the barrel has a distal portion that includes an inner post and an outer race that define a cavity. A proximal portion of the barrel is configured for receipt of a plunger. A needle is mounted with the inner post of the barrel and has a distal end. A tubular shield is mounted for slidable movement within the cavity of the barrel between a retracted position whereby the distal end of the needle is exposed, and an extended position whereby the distal end of the needle is covered. The shield includes a stability ring that is configured for adding structural integrity to the shield. A tubular lock insert is mounted with the inner post such that the shield is slidably movable along an outer surface of the insert. The lock includes a plurality of tangs disposed circumferentially thereabout, whereby the tangs are in substantial alignment with the outer surface of the insert during slidable movement of the shield. The tangs are biased radially outward to inhibit proximal movement of the shield in the extended position. The insert further includes a distal stop configured to inhibit distal movement of the shield.

In yet another alternative embodiment, a safety apparatus is provided in accordance with the principles of the present disclosure. The safety apparatus includes a first tubular member having a needle mounted therewith. A second tubular member is mounted with the first tubular member. A shield is movable between a first position whereby the needle is exposed and a second and third position whereby the needle is covered. The third position provides tactile feel of the shield placement. A lock is mounted with the first tubular member such that the second tubular member is slidably movable along an outer surface of the lock.

BRIEF DESCRIPTION OF THE DRAWINGS

The foregoing and other features and advantages of the present disclosure will be more fully understood from the following detailed description of the embodiments, taken in conjunction with the accompanying drawings in which.

DETAILED DESCRIPTION OF THE EMBODIMENTS

Figure 1:
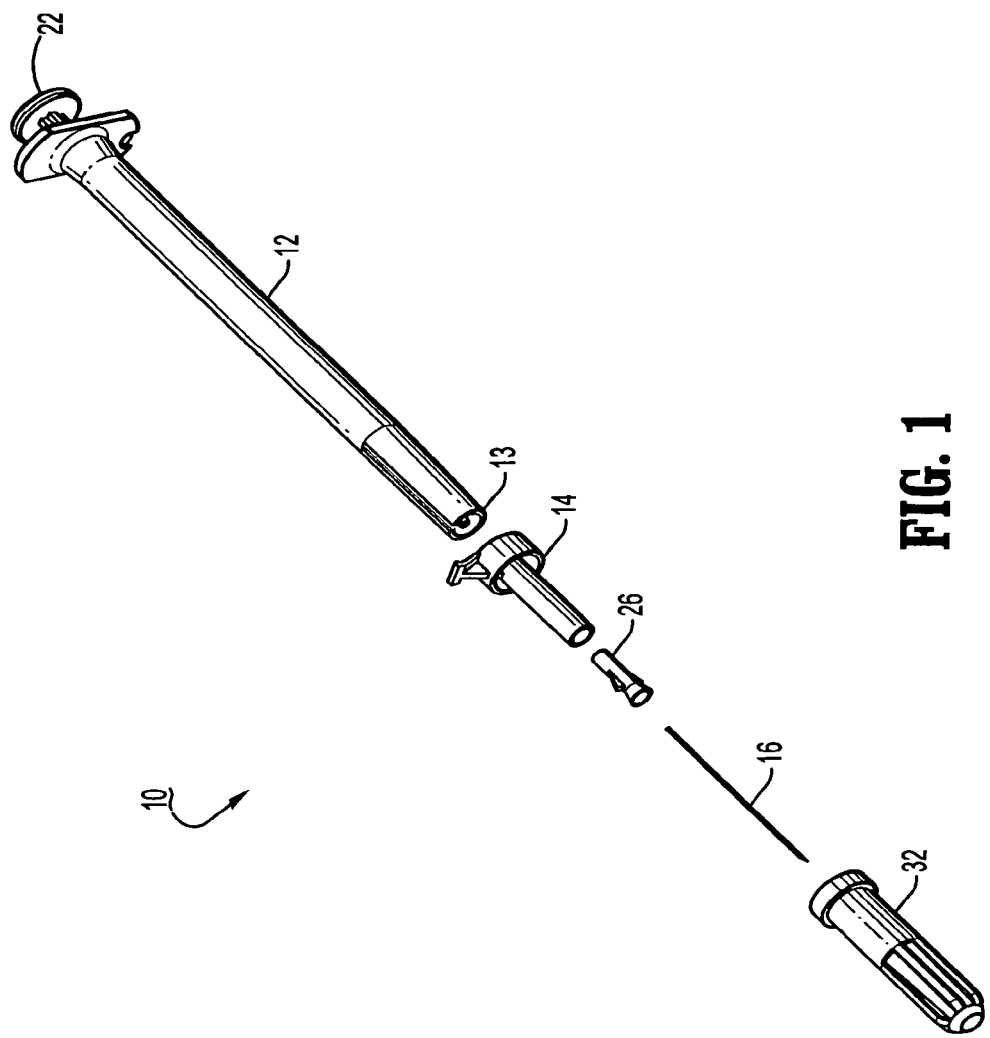
FIG. 1 is an exploded perspective view of a safety apparatus in accordance with the principles of the present disclosure.
Figure 2:
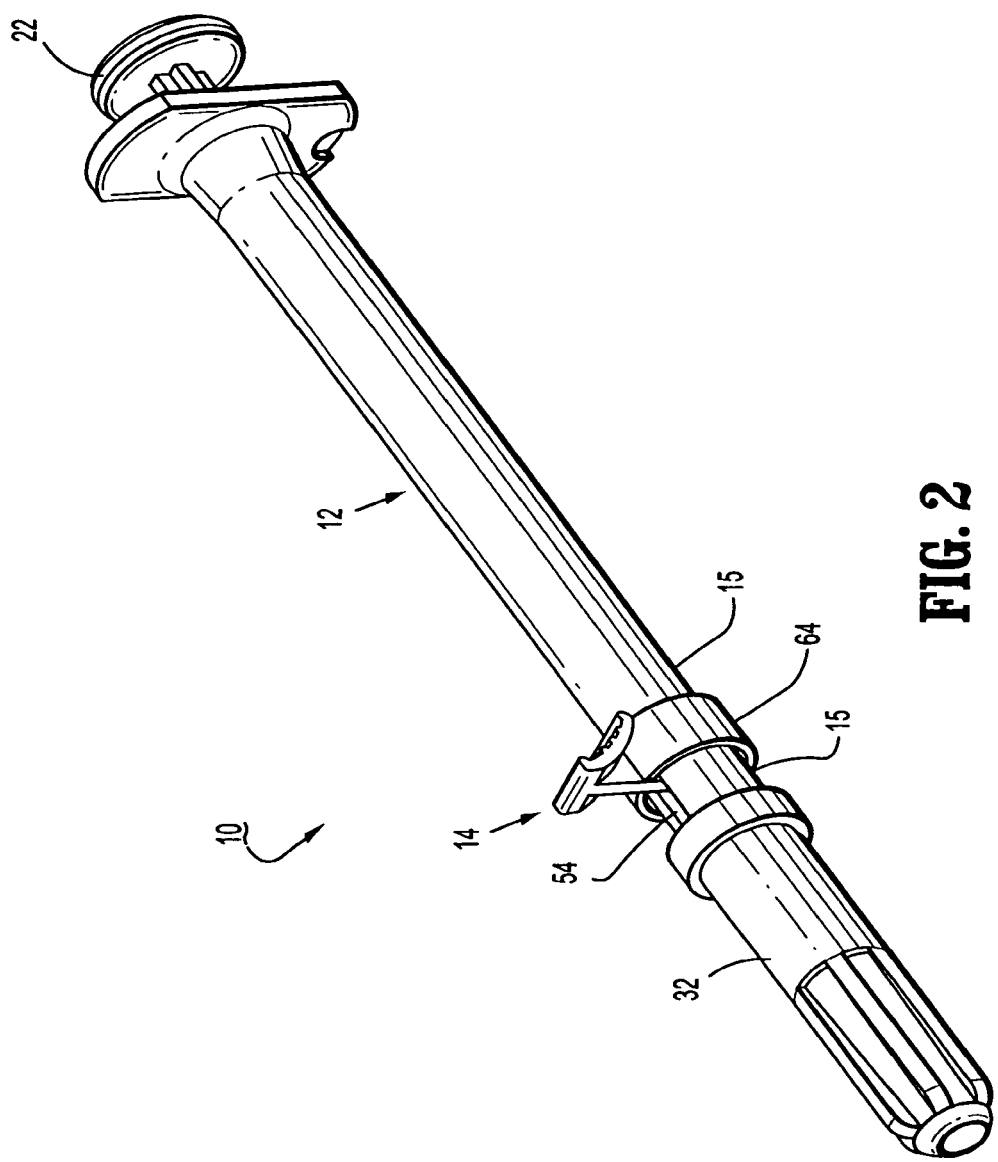
FIG. 2 is a perspective view of the apparatus shown in FIG. 1.

The embodiments of the safety apparatus and the methods of operation disclosed herein are discussed in terms of safety shields for medical needles for infusion of medication and nutrition fluids (via, for example, subcutaneous, intradermal, intravenous and/or intramuscular), and fluid collection, and more particularly, in terms of manually actuated safety shields that employ structure for positioning and locking a shield to minimize hazardous exposure to the needle cannula, for example, through an inadvertent needle stick. It is contemplated that the needle cannula may be shielded during use including storage, transport, fluid infusion, and/or collection, subsequent thereto, etc. It is envisioned that the present disclosure, however, finds application to a wide variety of cannula needles, including small needle applications and devices for the infusion of preventive medications, medicaments, and therapeutics to a subject. It is also envisioned that the present disclosure may be employed for collection of body fluids including those employed during procedures relating to phlebotomy, digestive, intestinal, urinary, and veterinary and the like. It is also contemplated that the safety apparatus may be utilized with other medical needle applications including feeding devices, phlebotomy devices, catheters, catheter introducers, guide wire introducers, spinal and epidural, biopsy, aphaeresis, dialysis, blood donor, Veress needles, Huber needles, and the like.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the safety apparatus. According to the present disclosure, the term "clinician" refers to an individual administering an infusion, performing fluid collection, installing or removing a needle cannula from a safety apparatus and may include support personnel.

The following discussion includes a description of the safety apparatus, in accordance with the present disclosure. Reference will now be made in detail to the embodiments of the disclosure, which are illustrated in the accompanying figures.

Turning now to the figures, wherein like components are designated by like reference numerals throughout the several views. Referring to FIGS. 1-10, there is illustrated a safety apparatus, such as, for example, a needle syringe or syringe 10. The syringe 10, as shown in FIGS. 1-5, includes a first tubular member, such as, for example, a syringe barrel or barrel 12 having a needle cannula or needle 16 mounted therewith via a needle mount 11. An open beveled portion 23 is disposed at a distal end of needle cannula 16. Needle cannula 16 is adhesively mounted to syringe barrel 12 at needle mount 11. Needle mount 11 includes nipple portion 19 (FIG. 3) for holding adhesive. Needle cannula 16 penetrates needle mount 11 generally between a depth of 0.010-0.020 inches. The adhesive is used to secure needle cannula 16 to needle mount 11. The adhesive forms a meniscus at nipple portion 19 and is interiorly displaced along the needle cannula shaft and the needle mount 11 about one-half of the needle penetration depth. A second tubular member, such as, for example, a tubular shield 14, is mounted with the barrel 12 and is movable from a retracted position (FIG. 3) whereby the needle 16 is exposed, to an extended position (FIGS. 4 and 5) whereby the needle 16 is covered. A lock, such as, for example, a tubular lock insert 26 is mounted with the barrel 12 such that the shield 14 is slidably movable along an outer surface 28 of the lock insert 26. The lock insert 26 includes arms or tangs 30 that are movable radially outward to fix the shield 14 in the extended position. It is contemplated that one or more tangs 30 may be employed with lock insert 26.

A removable sheath 32 (FIGS. 1 and 2) covers the needle 16 during transport and prior to use. The sheath 32 is ribbed to inhibit rolling when the syringe 10 is placed on a surface. Sheath 32 may include other structure configured to inhibit rolling such as projections, pads and the like. The sheath 32 is removably coupled to the syringe barrel 12. Sheath 32 is not in contact with shield 14 so as to inhibit inadvertent actuation of the syringe 10 when sheath member 32 is pulled off prior to use. Sheath 32 may be heat staked to syringe barrel 12 as a tamper evident feature as is known in the art.

Figure 3:
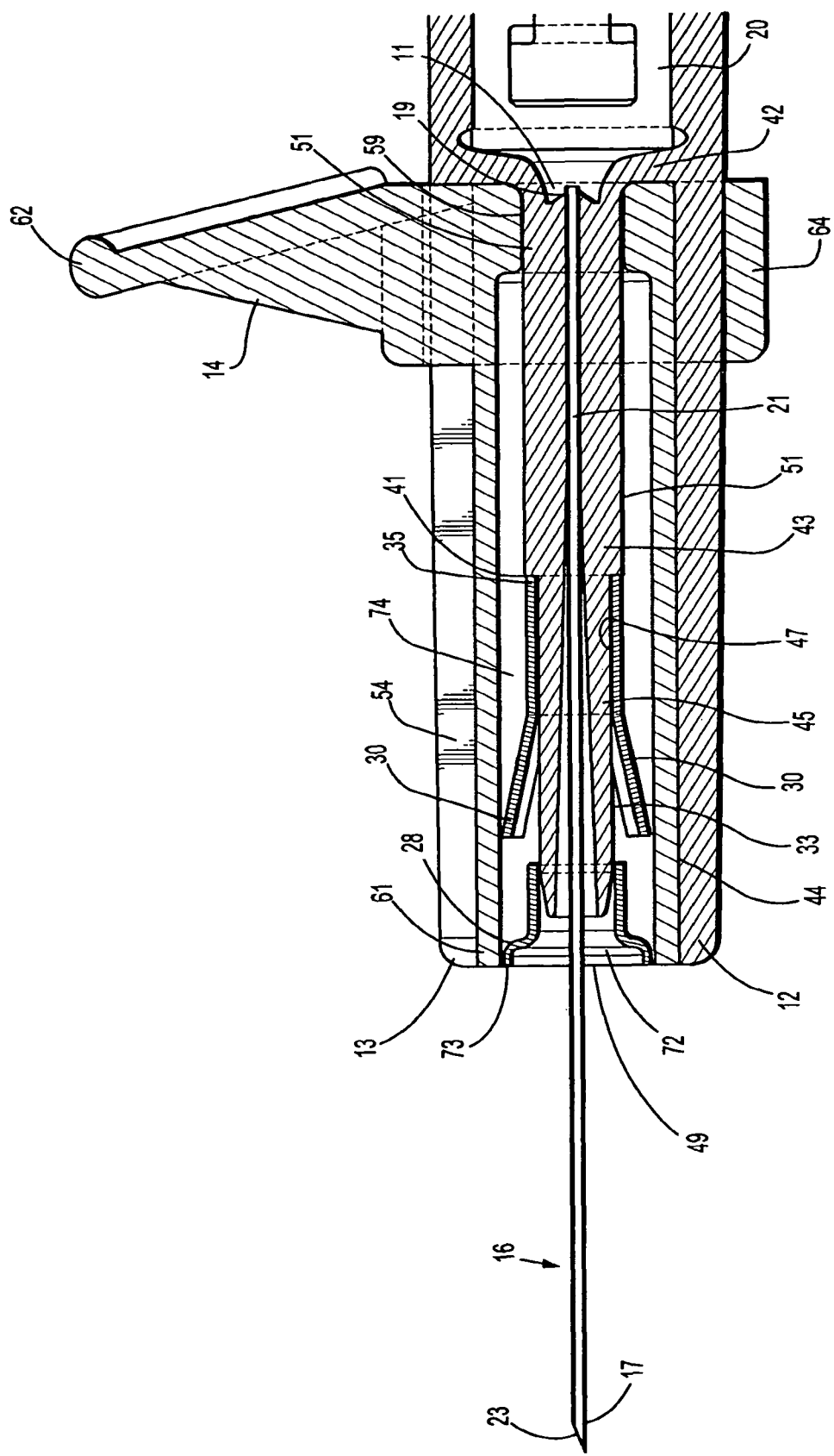
FIG. 3 is a cross-sectional side view of a distal portion of the apparatus shown in FIG. 1, in a ready-to-use position.
Figure 6:
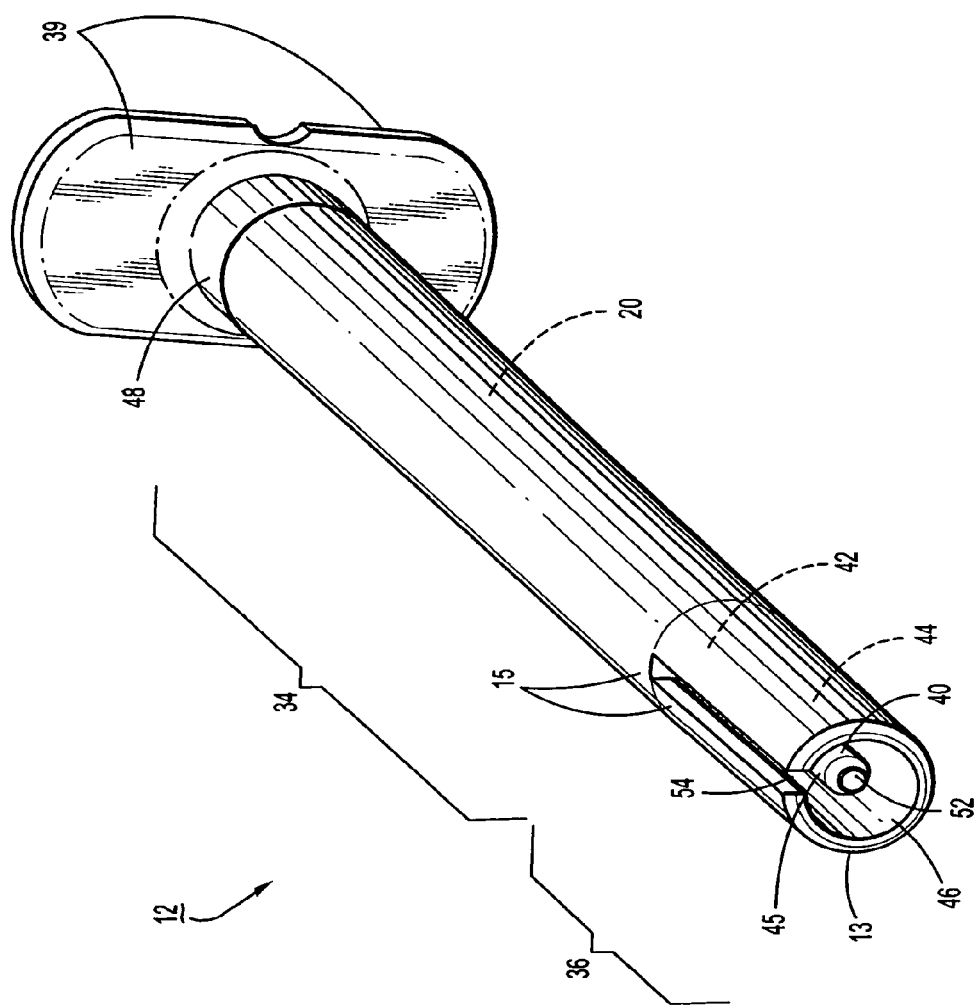
FIG. 6 is a perspective view of a barrel of the apparatus shown in FIG. 1.

A proximal portion 34 of the barrel 12, as shown in FIG. 6, defines a plunger cavity 20 configured for receipt of a plunger 22 (FIG. 1). Finger flanges 39 are disposed adjacent a proximal end 48 of the barrel 12 to facilitate manipulation of the syringe 10. A distal portion 36 of the barrel 12 includes a post 40 on which the shield 14 is slidably mounted and lock insert 26 is fixedly mounted. As shown in FIG. 3, the post 40 has a distal end 45 with an outer annular surface 47 and a proximal end 43 with an outer annular surface 51. The proximal end 43 has a slightly greater diameter than that of the distal end 45. A circumferential ridge 41 is defined by the juncture of the outer annular surface 47 and the outer annular surface 51.

Figure 4:
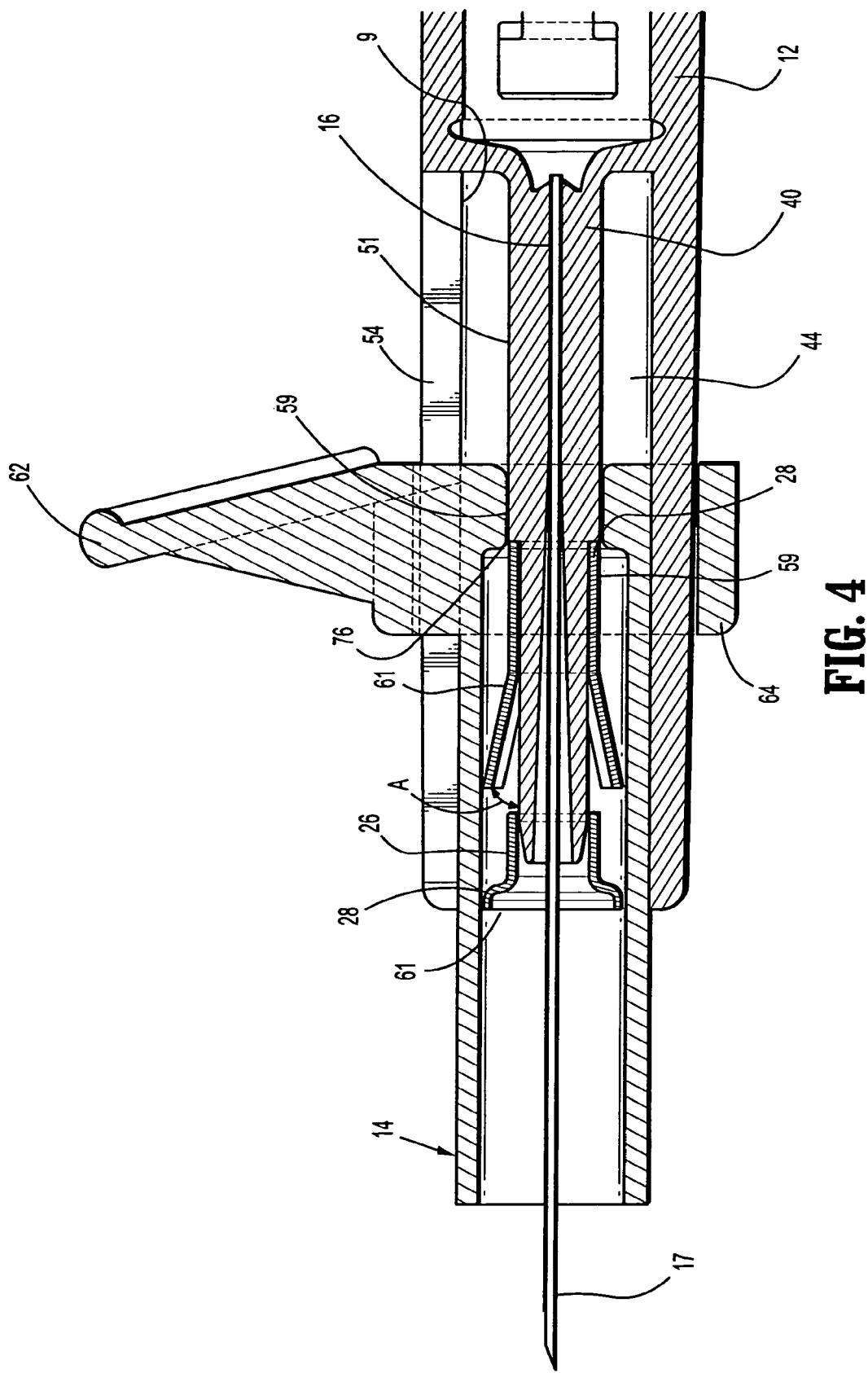
FIG. 4 is a cutaway cross-sectional side view of the distal portion of the apparatus shown in FIG. 1, in an extended position.
Figure 7:
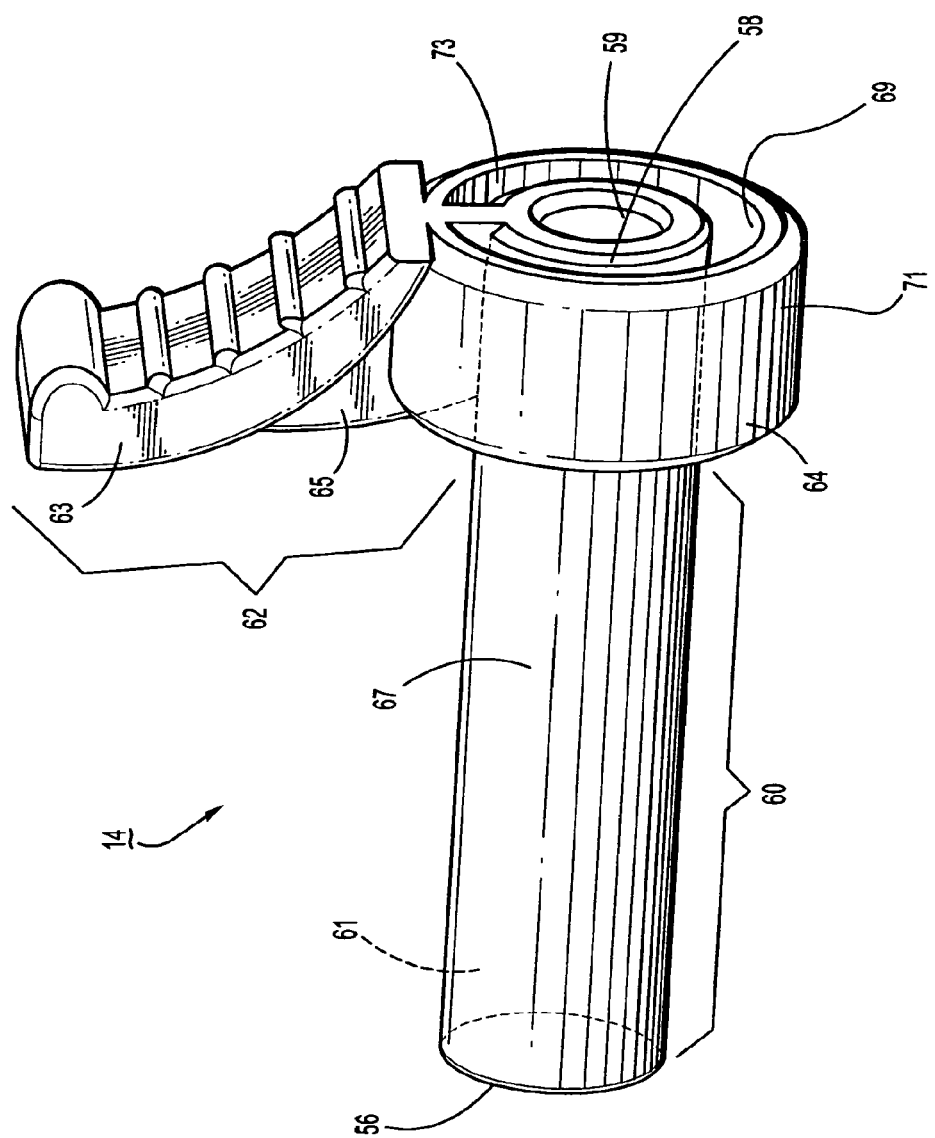
FIG. 7 is a perspective view of a shield of the apparatus shown in FIG. 1.

Barrel 12 further includes a channel such as, for example, race 46. The race 46 and post 40 define a cavity 44 configured for slidable movement of the shield 14 (FIG. 7). The race 46 and post 40 guide and support the shield 14 during travel in the cavity 44 and inhibit free play between the components. The cavity 44, as shown in FIGS. 3 and 4, has a tubular configuration and is bound longitudinally by a closed proximal end 42 and an open distal end 49. Cavity 44 has a circular cross section and is bound cross sectionally by the inner circumference 9 of the barrel 12 and the outer annular surfaces 47, 51 of the post 40. The cavity 44 may have alternative geometries to facilitate movement of the shield 14, for example, the cavity 44 may have an oval, tubular, hollow, or other polygonal cross section. The cavity 44 may also be concentric with shield 14. A longitudinal slot 54 extends from a distal end 13 of the barrel 12 along an outer wall 15 thereof. The slot 54 is configured to guide movement of the shield 14, as explained in greater detail below. The post 40 defines a needle cavity 52 that engages an outer surface of the needle 16 for support thereof. A proximal end (not shown) of the needle 16 extends into the plunger cavity 20 for fluid communication therewith. In addition, plunger cavity 20 is in fluid communication with beveled portion 23, thereby permitting fluid stored in plunger cavity 20 to be communicated through needle cannula 16 and beyond its distal end.

The shield 14, as shown in FIG. 7, is configured for telescopic mounting within the cavity 44 of the syringe barrel 12. It is contemplated that the shield 14 may include a tube portion 60 configured for covering the needle 16 and having an inner surface 61. A proximal end 58 of the tube 60 has a narrowed inner surface 59. A circumferential ridge 76 (FIG. 4) is defined by the juncture of the inner surface 61 and the narrowed inner surface 59. An actuator 62 is disposed with the tube 60 for causing slidable movement of the shield 14. The actuator 62 includes a neck 65 that extends radially from the proximal end 58 of the tube 60. A ribbed finger pad 63 is disposed with the neck 65.

The shield 14 includes a stability member, such as, for example, a stability ring 64 to provide additional stability during axial movement of the shield 14 with respect to the barrel 12 of the syringe 10. The stability ring 64 adds structural integrity to keep the shield 14 firmly in place when it is locked in the fully extended position. Ring 64 surrounds the tube 60 near the proximal end 58 such that a gap 73 exists between the shield's outer wall 67 and the ring 64. The ring 64 intersects the actuator 62 and includes an inner surface 69 and an outer surface 71. The stability member 64 may have alternate geometries configured to provide stability and/or structural integrity.

Figure 8A:
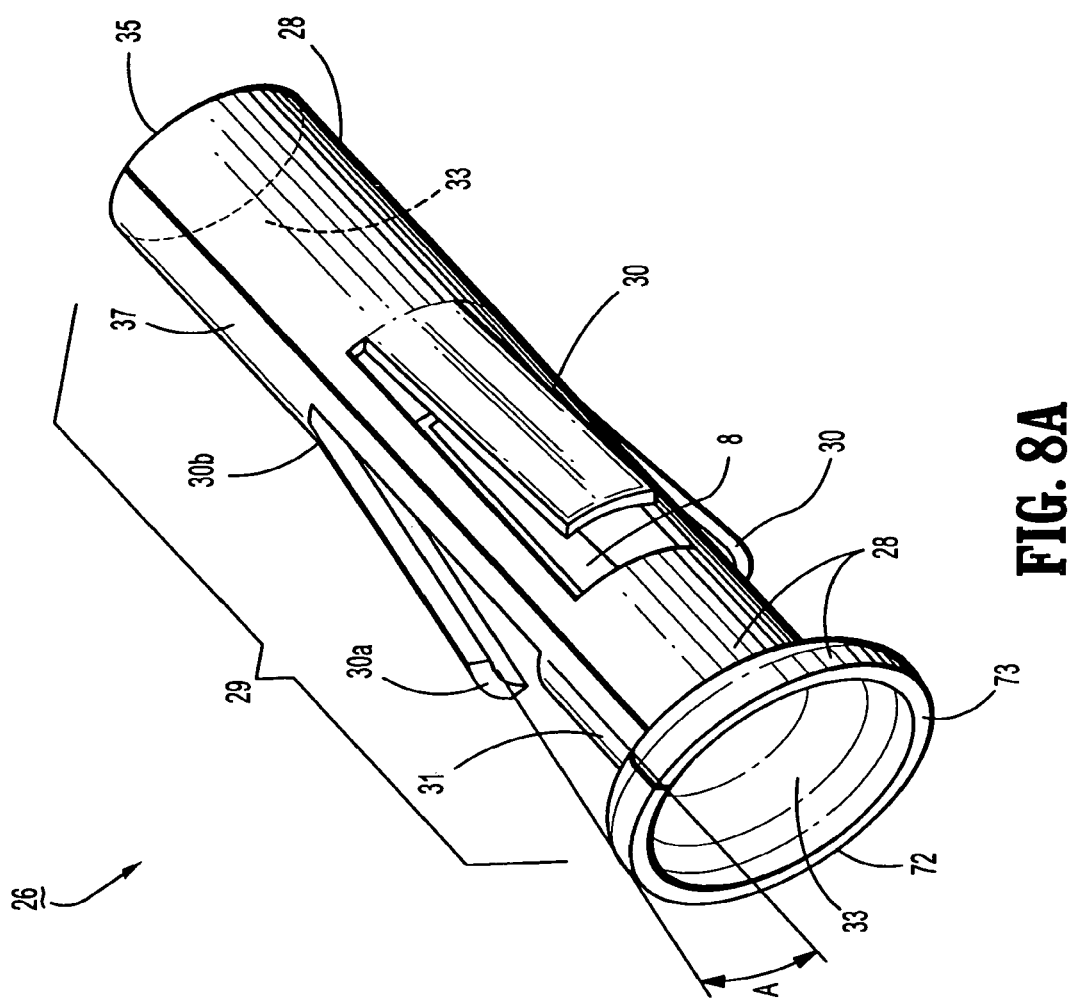
FIG. 8A is a perspective view of an insert of the apparatus shown in FIG. 1.

The lock insert 26, as shown in FIG. 8A, is configured for mounting on the post 40. As will be later explained in greater detail, the lock insert 26 retains the shield 14 in a "ready-to-use" position and inhibits distal sliding of the shield 14. The lock insert 26 also inhibits the shield 14 from traveling proximally from a fully shielded position. The lock insert 26 has annular inner surfaces 33 and annular outer surfaces 28, and includes a tubular lock sleeve 29 having a distal end 31 and a proximal end 37. A stop member, such as, for example, a protruding rim or flange 72 is disposed at the distal end 31 and includes a circumferential edge 73. The proximal end 37 includes a circumferential edge 35.

The lock insert 26 includes a projection member, such as for example, a tang 30 that is movable radially outward to fix the shield 14 in the extended position. One or a plurality of tangs 30 may be employed. The tang 30 is disposed circumferentially about the outer surface 28 of the lock insert 26 intermediate the distal and proximal ends 31, 37 of the sleeve 29. Tang 30 is cantilevered from sleeve 29 through cutout 8 in the surface 28. The tang 30 is pivotable from its proximate edge 30b. Tang 30 is biased for radially outward movement such that its distal end 30a tends to extend above the surface 28 to define an angle A therewith. When compressed, the tang 30 pivots into substantial alignment with the surface 28. The lock insert 26 may include other structure configured to lock the shield 14 such as, stops, protuberances and the like. Operation of the lock insert 26 is described below in more detail.

Figure 8B:
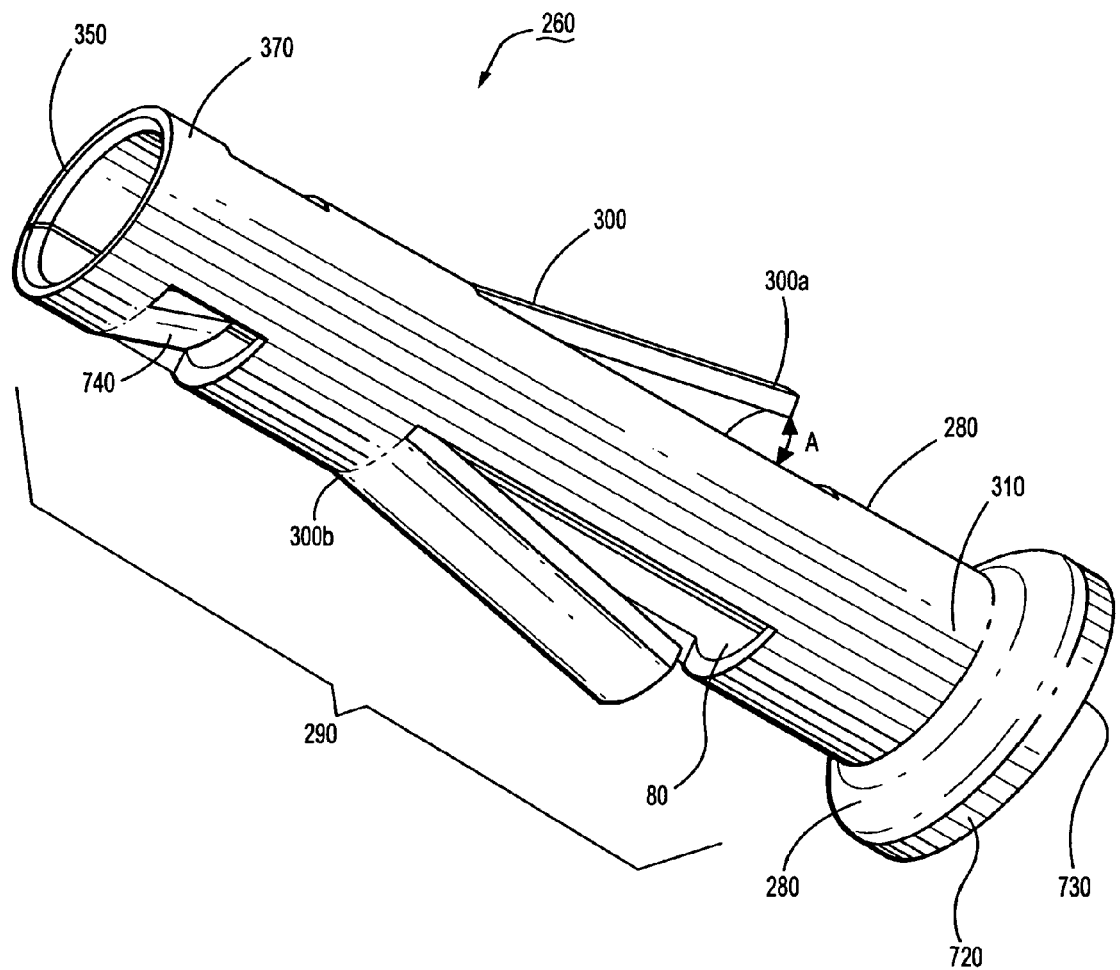
FIG. 8B is a perspective view of an alternate insert of the apparatus in accordance with the principles of the present disclosure.
Figure 8C:
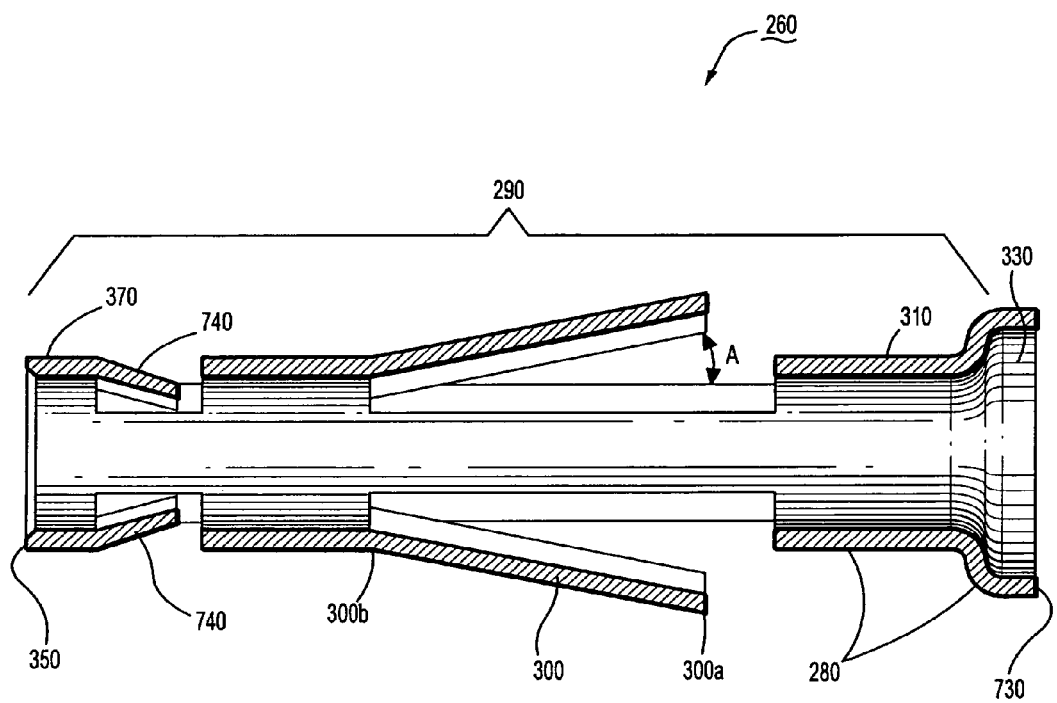
FIG. 8C is a cross-sectional view of the insert shown in FIG. 8B.

With reference to FIGS. 8B and 8C, where like reference numerals are used to designate like elements for the sake of simplicity of explanation, there is disclosed an alternative embodiment of lock insert 26. Lock insert 260 is configured for mounting on post 40 and is designed to retain the shield 14 (FIG. 4) in a "ready-to-use" position and inhibits distal sliding of the shield 14. The lock insert 260 also inhibits the shield 14 from traveling proximally from a fully shielded position. The lock insert 260 has inner annular surfaces 330 and outer annular surfaces 280 and includes a tubular lock sleeve 290 having a distal end 310 and a proximal end 370. A flange 720 is disposed at the distal end 310 and includes a circumferential edge 730. The proximal end 370 includes a circumferential edge 350.

The lock insert 260 includes a tang 300 that is movable radially outward to fix the shield 14 in the extended position. One or a plurality of tangs 300 may be employed. The tang 300 is disposed circumferentially about the outer surface 280 of the lock insert 260 intermediate the distal 310 and proximal 370 ends of the sleeve 290. Tang 300 is cantilevered from sleeve 290 through cutout 80 in the surface 280. The tang 300 is pivotable from its proximate edge 300b. Tang 300 is biased for radially outward movement such that its distal end 300a tends to extend above the surface 280 to define an angle A therewith. When compressed, the tang 300 pivots into substantial alignment with the surface 280. The lock insert 260 may include additional structure configured to lock the shield 14 such as projection member 740 that is disposed circumferentially about the outer surface 280 of the lock insert 260 and is biased radially inward to secure or fix the insert 260 to the outer surface 47 of the post 40 (FIG. 3). One or a plurality of projection members 740 maybe employed with insert 260.

It is contemplated that the lock inserts 26, 226 (discussed in detail hereinbelow), and 260 may be fabricated from metal or other durable material suitable for medical applications, such as, for example, stainless steel. More particularly, the lock inserts may be formed, for example, by a process known as progressive die forming wherein a die component combines a number of forming and stamping functions such as blanking, forming, flange forming, punching, and trimming into a single die. The metal blank that will ultimately form the lock inserts is fed into the die. Each time the die cycles, a stamping operation is made on the metal blank material and it is automatically advanced to the next position. Each station within the progressive die process serves to progressively form, the final lock inserts. Finally, the completed lock inserts 26, 226, and 260 are ejected from the end of the progressive die once all the operations have been completed.

The components of the safety apparatus can be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate.

The lock insert 26 is securely mounted, as shown in FIG. 3, on the distal end 45 of the post 40 via interference between an inner surface 33 of the lock sleeve 29 and an outer surface 47 of the post 40. To further secure the lock insert 26 on the post 40, the circumferential edge 35 of the lock insert 26 abuts the circumferential ridge 41 of the post 40. In this regard, the outer surface 28 of the lock sleeve 29 is substantially aligned with the outer surface 51 along the proximal end 43 of the post 40. A distal edge 73 of the flange 72 is substantially aligned with the distal end 13 of the barrel 12. The tangs 30 extend at an angle from the outer surface 28 of the lock sleeve 29, as described above.

The assembly of the syringe 10 can be performed sequentially. For example, shield 14 may be inserted into the distal end of syringe barrel 12 followed by lock insert 26 and then finally assembly of needle cannula 16 to syringe barrel 12. The needle cannula 16 can be attached to syringe barrel 12 at any point during the assembly procedure.

The operation of the syringe 10 during a medical procedure will now be described. Initially, proper preparation and sterilization of the syringe 10 is performed (not shown), and the sheath 32 is removed. The shield 14, as shown in FIG. 3, is mounted telescopically on the post 40 in the "ready-to-use" (i.e. retracted) position whereby the distal portion 17 of the needle 16 is exposed. The narrowed end 58 of the shield 14 is adjacent the proximal wall 42 of the cavity 44 and the narrowed inner surface 59 of the shield 14 is contiguous with the outer surface 51 of the post 40. The distal inner surface 61 of the shield 14 is proximate the outer surface 28 of the lock flange 72.

There is a gap 74 between the inner surface 61 of the shield 14 and the outer annular surfaces 47, 51 of the post 40. The tang 30 is biased for radially outward movement and thus extends in the gap 74 such that distal end 30a is proximate the inner surface 61. The stability ring 64 associated with the shield 14 is disposed circumferentially about the outside wall 15 of the barrel 12. The actuator 62 of the shield 14 extends through the slot 54. The lock insert 26 mounted within the shield 14 retains the shield 14 in the ready-to-use position and inhibits distal sliding thereof. The lock flange 72 is substantially aligned with the distal end 56 of the shield 14.

After completing the medical procedure, the clinician manipulates the shield 14 forward via one-handed operation to cover the distal end 17 of the needle 16, as shown in FIG. 4. This is accomplished using the thumb or index finger to urge the actuator 62 distally along the slot 54. Alternatively, a corner of a rigid surface such as a table or counter top may be used to manipulate the shield 14. Both techniques provide relative movement between the shield 14 and the barrel 12. As the shield 14 moves forward, the narrowed interior surface 59 of the shield 14 slides along the outer surface 51 of the post 40, and along the outer surface 28 of the lock insert 26. The inner surface 61 of the shield 14 slides along the outer surface 28 of the flange 72.

Figure 5:
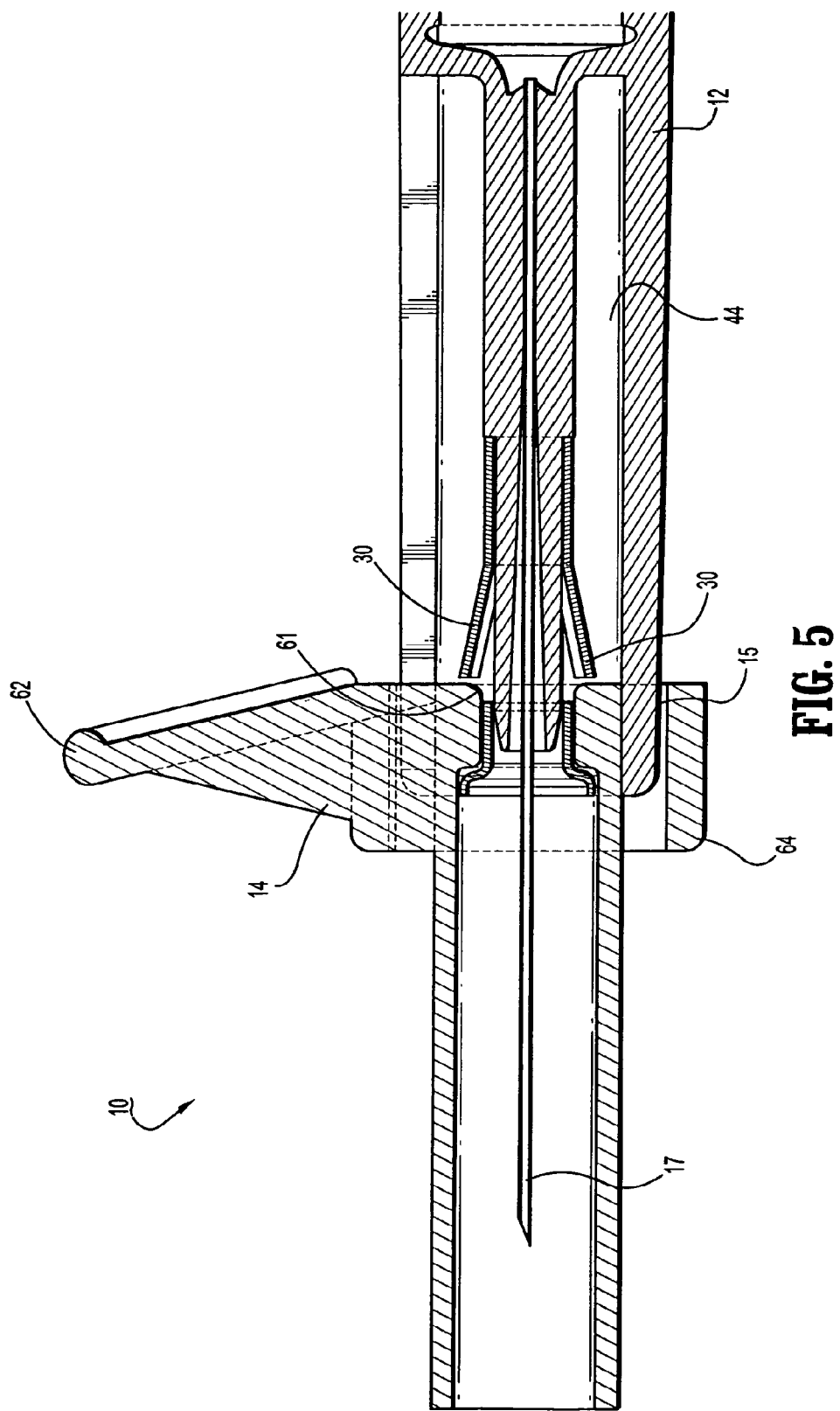
FIG. 5 is a cutaway cross-sectional side view of the distal portion of the apparatus shown in FIG. 1, in a locked position.
Figure 9:
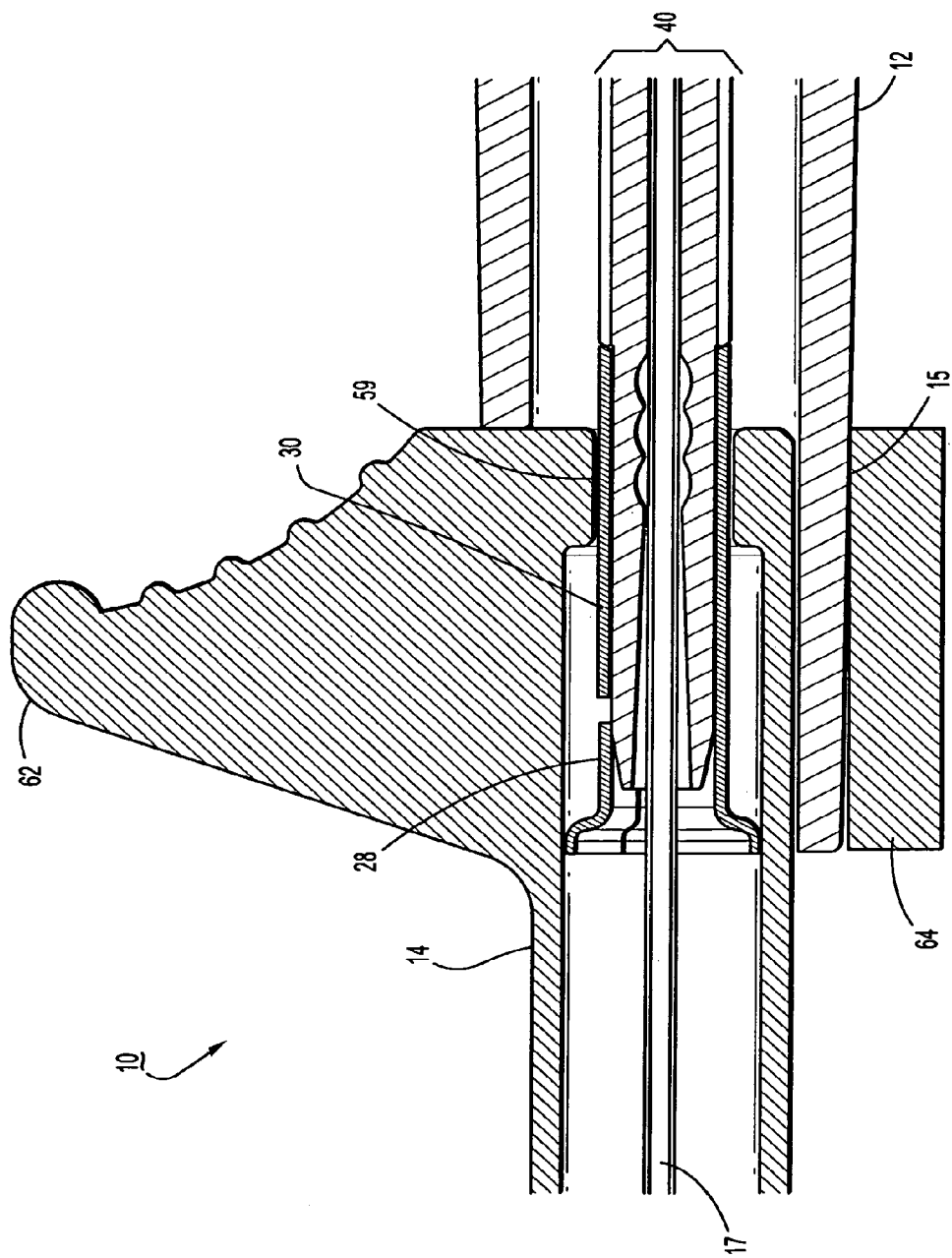
FIG. 9 is a cutaway side cross-sectional view of the distal portion of the apparatus shown in FIG. 1, in an extended position.

As the shield 14 is moved further, as shown in FIG. 9, the narrowed inner surface 59 of the shield 14 slides over the tangs 30. Consequently, the tangs 30 compress into substantial alignment with the lock surface 28 such that the angle A becomes substantially zero. After the narrowed surface 59 of the shield 14 slides past the compressed tang 30, as shown in FIG. 5, the tang 30 (being biased for radially outward motion) snaps back outwardly. That is, the tang 30 pivots from its proximal end 30b such that the distal end 30a extends into the gap 74 to oppose any proximal (backward) movement of the shield 14. Locking of the shield 14 in this way disables the syringe 10 and inhibits re-exposure of the needle tip 17.

Figure 10:
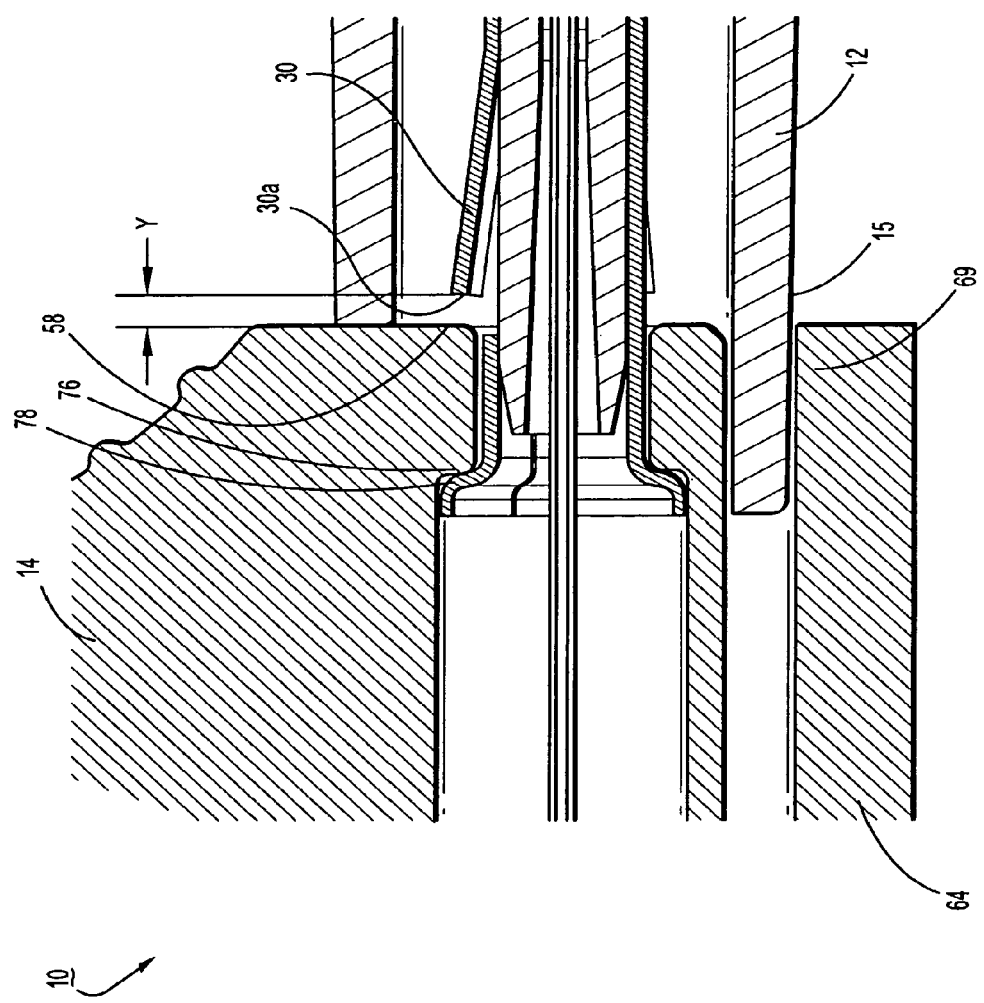
FIG. 10 is an enlarged cutaway side cross sectional view of the distal portion of the apparatus shown in FIG. 1, in a fully extended position.
Figure 11A:
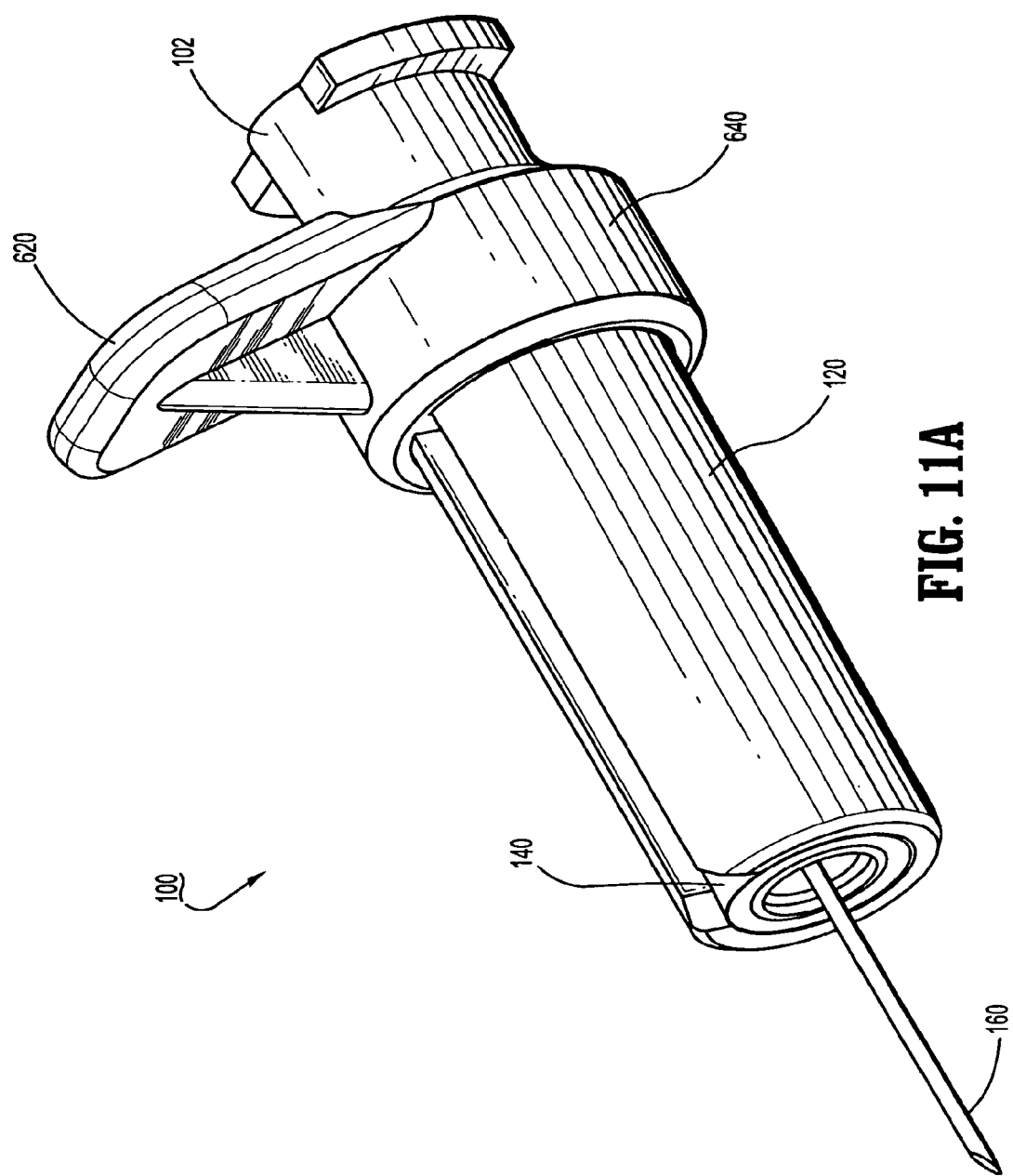
FIGS. 11A and 11B are perspective views of an alternative embodiment of the apparatus in accordance with the principles of the present disclosure.
Figure 11B:
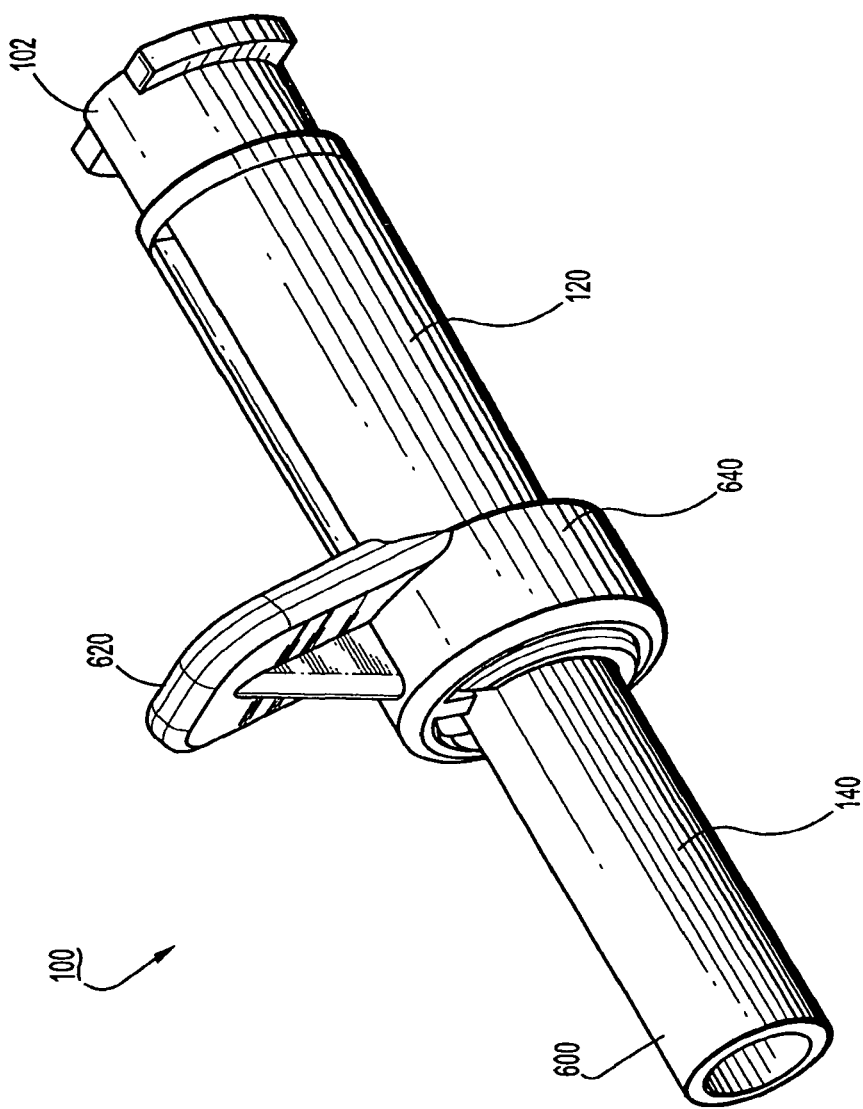
Figure 12A:
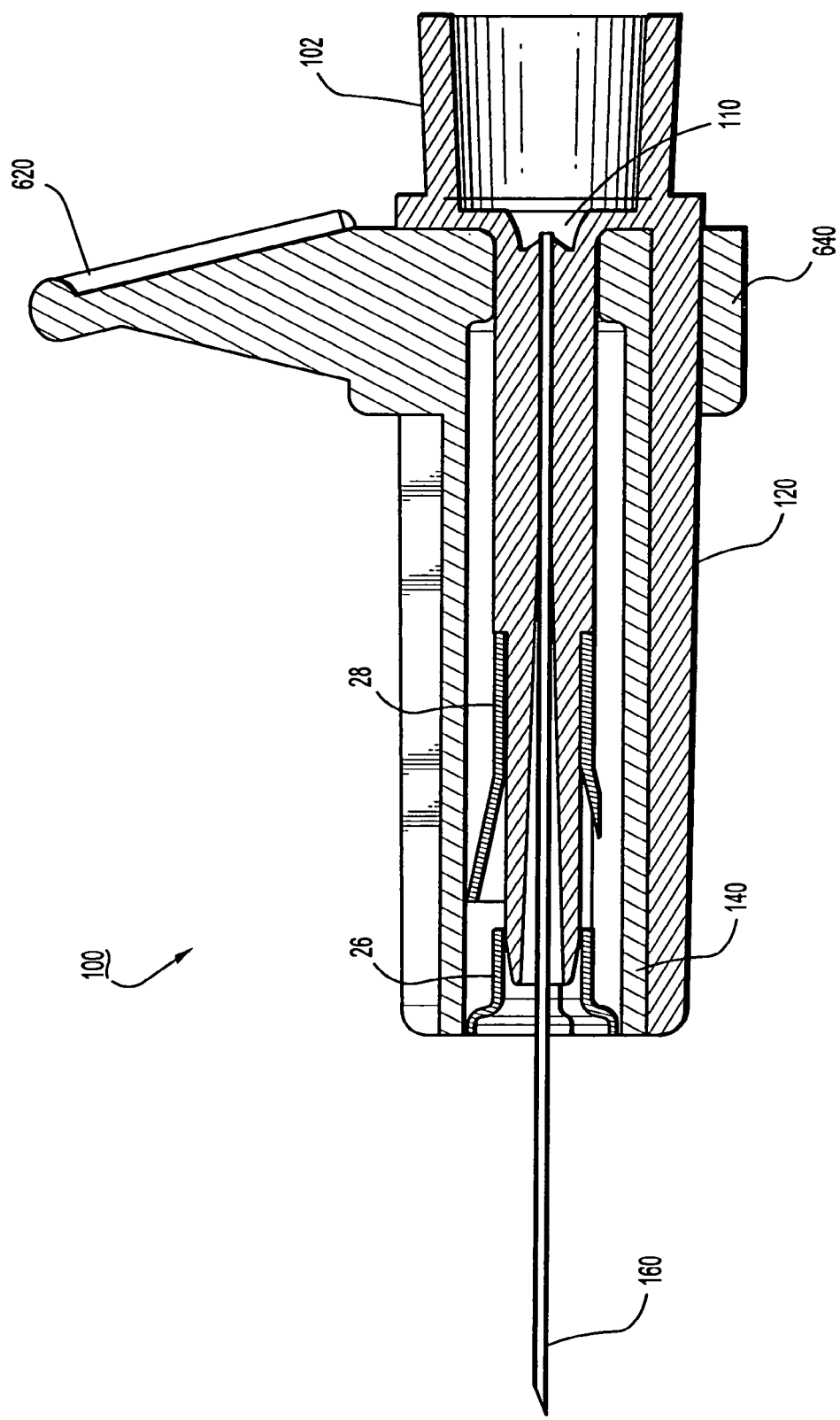
FIGS. 12A and 12B are respective cross-sectional views of the apparatus shown in FIGS. 11A and 11B.
Figure 12B:
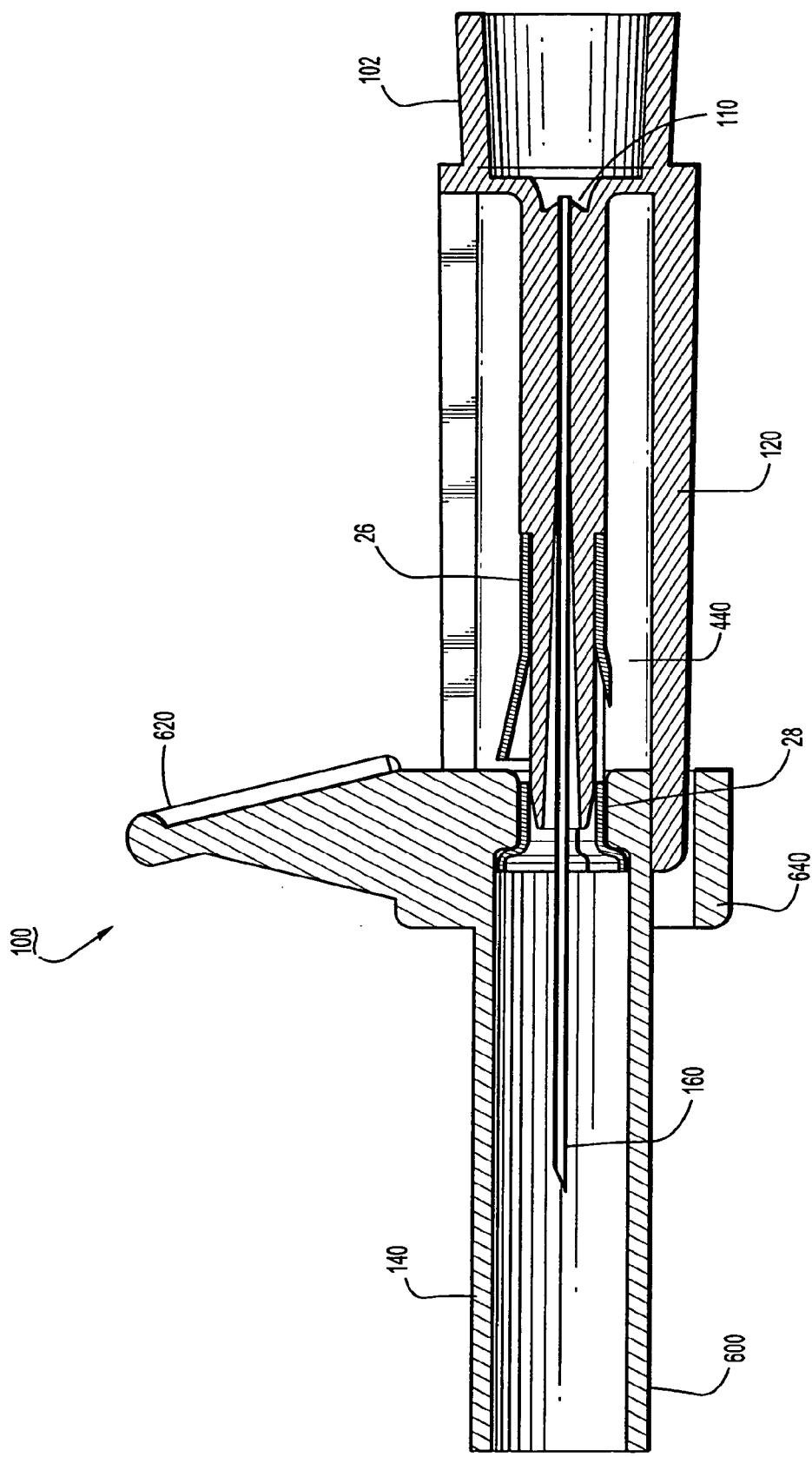

A gap Y, as shown in FIG. 10, between the distal end 30a of the tang 30 and the proximal end 58 of the shield 14 provides free play therebetween. This free play enables movement of the shield 14 to provide a tactile indicator or feedback that the shield 14 is in the fully extended position. The circumferential ridge 76 at the shield 14 interior abuts a proximal ridge 78 at the lock flange 72 to inhibit the shield 14 from traveling too far distally. The inner surface 69 of the stability ring 64 engages the outer wall 15 of the barrel 12 for added structural integrity when the shield 14 is in the fully extended position.

As discussed above, the lock insert 26 disables the safety syringe 10 by inhibiting the shield 14 from traveling proximally via tangs 30, from a fully shielded position, to re-expose needle cannula 16. The lock insert 26 defines the gap Y between a distal end 30a of the tangs 30 and the shield 14 to provide free play therebetween. This free play enables slight movement of the shield 14 to provide a tactile indicator that the shield 14 is in the fully shielded position. The lock insert 26 also inhibits the shield 14 from traveling too far distally via circumferential ridge 76 and proximal ridge 78 at the lock flange 72 that act as a forward stop. The metal lock insert 26, tangs 30, and forward stop act to inhibit movement of the shield 14 in a fully shielded position.

A desirable advantage of the combination of the gap Y between the lock insert 26 and the proximal end 58 of the shield 14 is that it minimizes lock insert 26 from kicking out through the slot 54 during a catastrophic failure of the safety syringe 10. In such a failure, safety syringe 10 would remain in its safe position. Moreover, if the safety syringe 10 were to experience a catastrophic failure, where the syringe 10 was subject to forces that would lead to breaking of the syringe 10, the syringe 10 is so designed that the proximal end of the needle cannula 16 and shield 14 would still remain in its safe position shielding the needle cannula 16.

The above-described configuration advantageously inhibits removal of the shield 14 from the syringe barrel 12. Further, mounting the shield 14 within the outer diameter of the syringe barrel 12 keeps the syringe profile extremely low. This configuration avoids impedance of administration of fluids via medical needle syringe 10, during, for example, low-angle subcutaneous injections, etc. Since the shield 14 is captured by both the inner post 40 and the outer race 46, a no-wobble, smooth extension of the shield 14 over the needle 16 is assured. The entire shield 14 is held forward of the syringe barrel 12 such that the graduations or other markings on the barrel 12 are not obscured. Other key advantages include one-hand activation of the medical needle syringe 10 and inclusion of the stability ring 62 for additional structural integrity when the shield 14 is in the fully extended or locked position.

With reference to FIGS. 11A, 11B and 12A, 12B, where like reference numerals are used to designate like elements for the sake of simplicity of explanation, there is disclosed an alternative embodiment of a safety needle apparatus or needle syringe 100 including a distally mounted standard luer fitting 102 for attachment to a syringe barrel (not shown). Similar to syringe 10, safety needle apparatus 100 includes a barrel component 120 having a needle cannula or needle 160 mounted therewith via a needle mount 110. A tubular shield 140 is mounted with the barrel 120 and is moveable from a retracted, "ready-to-use" position (FIGS. 11A and 12A) whereby the needle 160 is exposed, to an extended, "safety" position (FIGS. 11B and 12B) whereby the needle 160 is covered. A lock insert 26 is mounted with the barrel 120 such that the shield 140 is slidably movable along an outer surface 28 of the lock insert 26. A removable sheath, similar to sheath 32 (FIGS. 1 and 2), covers the needle 160 during transport and prior to use.

The shield 140 is configured for telescopic mounting within the cavity 440 (FIG. 12) of the barrel 120. The shield 140 includes a tube portion 600 configured for covering the needle 160 after as surgical procedure. An actuator 620 is disposed with the tube 600. The shield 140 includes a stability member, such as, for example, a stability ring 640 to provide additional stability during axial movement of the shield 140 with respect to the barrel 120 of the safety needle 100. The stability ring 640 adds structural integrity to keep the shield 140 firmly in place when it is locked in the fully extended position.

Figure 13A:
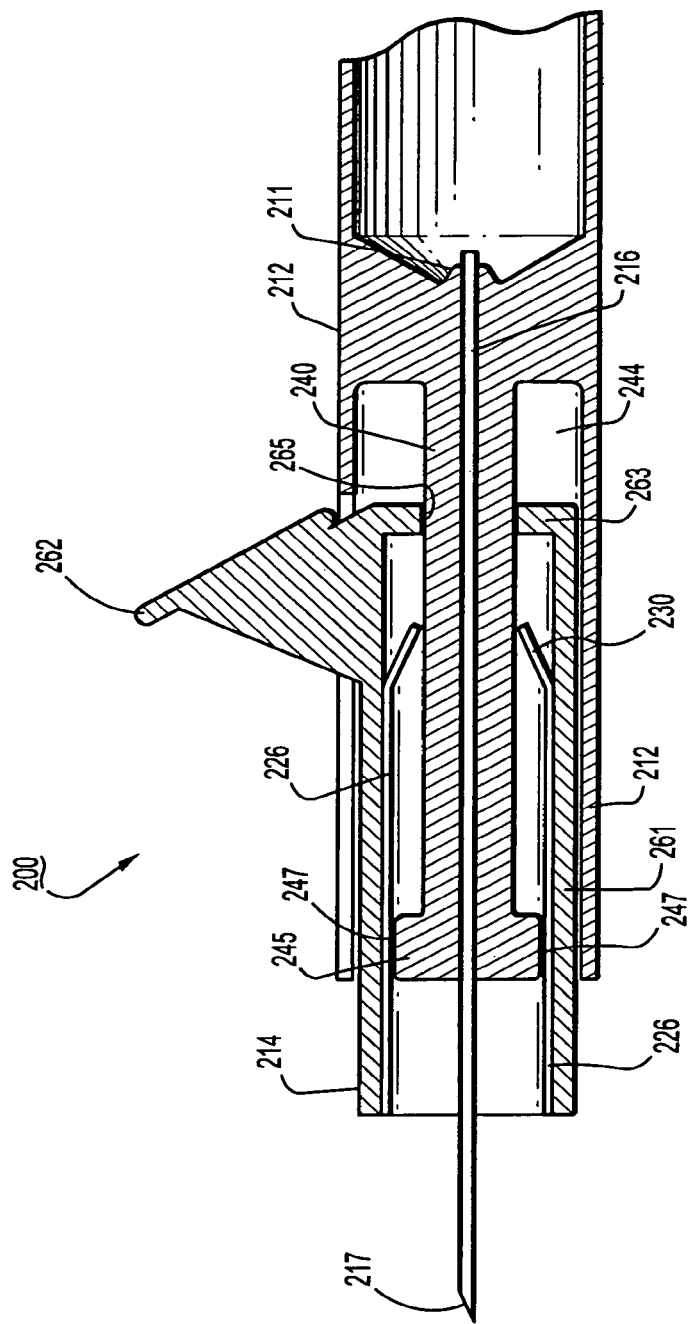
FIG. 13A is a cross-sectional side view of an alternative embodiment of the apparatus in accordance with the principles of the present disclosure, in a partially extended position.
Figure 13B:
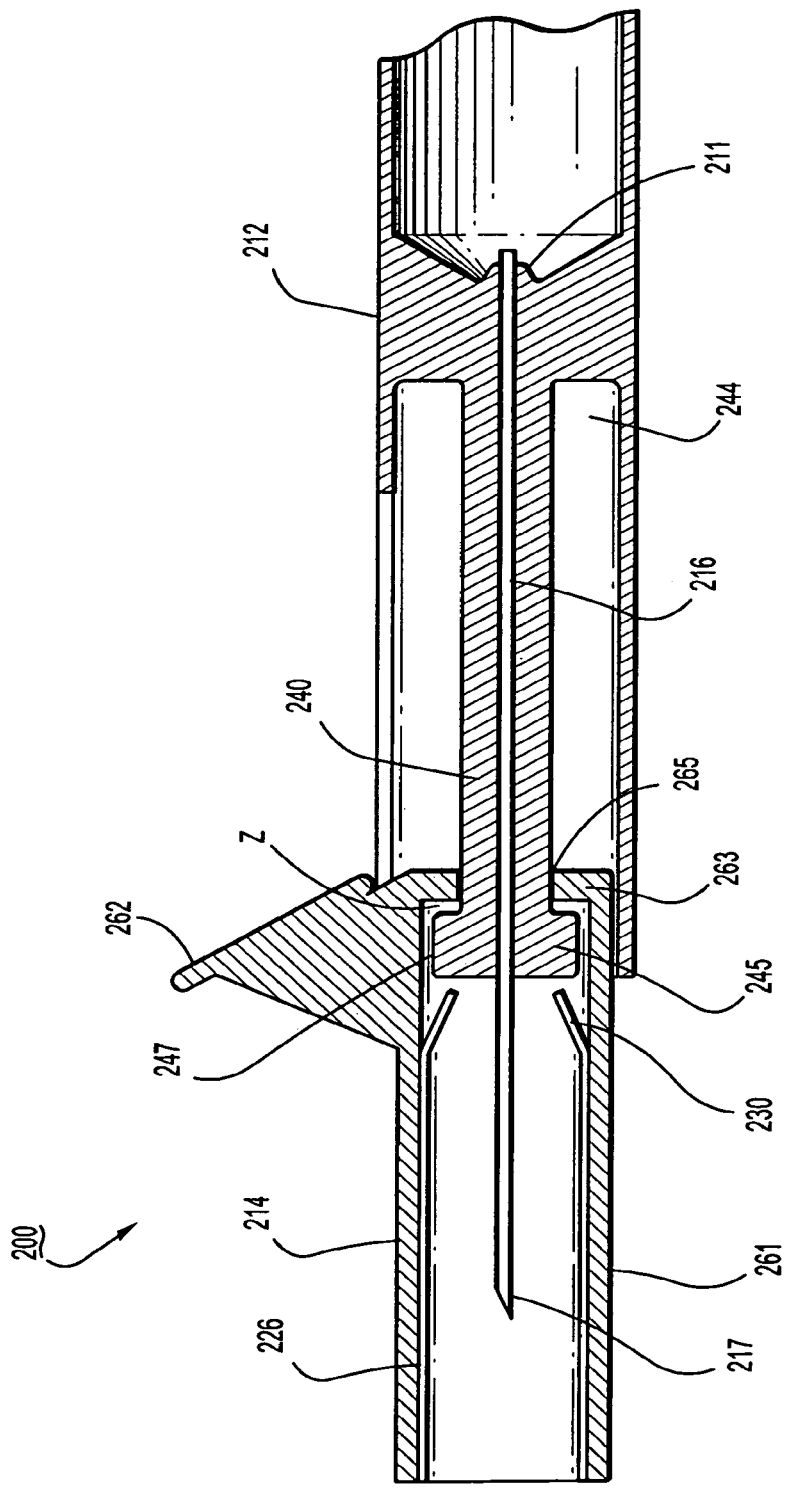
FIG. 13B is a cross-sectional side view of the apparatus shown in FIG. 13A, in an extended, locked position.

Now referring to FIGS. 13A and 13B, where like reference numerals are used to designate like elements for the sake of simplicity of explanation, there is disclosed an alternative embodiment of a safety needle apparatus or needle syringe 200 including a barrel component 212 having a needle cannula or needle 216 mounted therewith via a needle mount 211. A tubular shield 214 is mounted with the barrel 212 and is moveable from a retracted, "ready-to-use" position (not shown) and a partially extended position (FIG. 13A) whereby the needle 216 is exposed, to an extended, "safety" or "locked" position (FIG. 13B) whereby the needle 216 is covered. A lock insert 226 having at least one radially inward biased tang member 230 (two tang members 230 are shown) is mounted with the tubular shield 214 such that the lock insert 226 and tubular shield 214 are slidably movable with respect to the barrel component 212. A removable sheath, similar to sheath 32 (FIGS. 1 and 2), covers the needle 216 during transport and prior to use.

Barrel component 212 further includes a post member 240 onto which the shield 214 and lock 226 are slidably mounted. The post 240 has a distal end 245 with an extended annular surface 247. The distal end 245 has a greater diameter than that of the post 240 for engaging the tang members 230 of lock insert 226 and a proximal end wall 263 of the shield 214 (as discussed below).

The shield 214 and lock insert 226 are configured for telescopic mounting within a cavity 244 of the barrel 212. The shield 214 includes a tube portion 261 configured for covering the needle 216 after a surgical procedure. An actuator 262 is disposed with the tube portion 261 for aiding in distal movement of the shield 214. Shield 214 further includes a proximal end wall 263 having a centrally disposed through hole 265 for sliding along the post 240 of barrel 212. Proximal end wall 263 provides additional stability during axial movement of the shield 214 with respect to the barrel 212. The proximal end wall 263 adds structural integrity to keep the shield 214 firmly in place when it is locked in the fully extended position (FIG. 13B).

The operation of the safety needle apparatus 200 is similar to operation of other safety needle apparatuses (i.e. needle syringes 10 and 100) described herein. After completing the medical procedure, the clinician manipulates the shield 214 forward (i.e. distally) to cover the distal end 217 of the needle 216. As the shield 214 and lock insert 226 move forward, the interior surface of the shield 214 and tangs 230 of the lock insert 226 slide along the outer surface of the post 240. As the shield 214 is moved further, the tangs 230 are slid over the distal end 245 and extended annular surface 247 of the post 240. Consequently, the tangs 230 compress for allowing the enlarged annular surface 247 of the post 240 to pass the compressed tangs 230. The tangs 230 (being biased for radially inward motion) snap back inwardly once the shield 214 and tangs 230 are past the annular surface 247 of the post 240 (FIG. 13B). That is, the tangs 230 pivot such that the tangs 230 extend inwardly to oppose any proximal (i.e. backward) movement of the shield 214. Locking of the shield 214 in this way disables the needle apparatus 200 and inhibits re-exposure of the needle tip 217.

With reference to FIG. 13B, the proximal end wall 263 of the shield 214 abuts the distal end 245 of the post 240 to inhibit the shield 214 from traveling too far distally. Additionally, a gap Z, between the proximal end wall 263 of the shield 214 and the distal end 245 of the post 240 provides free play therebetween. This free play enables movement of the shield 214 to provide a tactile indicator or feedback that the shield 214 is in the fully extended position. The invention of the present disclosure may be embodied in other specific forms without departing from the spirit or essential characteristics thereof. For example, the first and second members can encompass varied cross-sectional shapes, for example, oval and rectangular, as long as one of the first and second members is slidably movable relative to the other. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A surgical device comprising:
    a first member having a cavity and a post disposed in the cavity;
    a second member slidably attached to the first member, the second member movable between a first position and a second position; and
    a lock disposed in the cavity, the lock including at least one arm, wherein axial movement of the second member from the first position to the second position moves the at least one arm towards the post, such that when the second member is in the second position a distal end of the at least one arm engages a surface of the second member and inhibits the second member from movement towards the first position;
    wherein an exterior surface of a distal end of the first member is exposed when the second member is in the first position such that direct contact with the distal end of the first member is permitted, and the exterior surface of the distal end of the first member is covered when the second member is in the second position such that the second member provides a barrier against direct contact with the distal end of the first member.

2. The surgical device of claim 1, wherein the at least one arm is radially biased towards an inner surface of the cavity.

3. The surgical device of claim 1, wherein the second member includes a proximal flange for engaging the distal end of the at least one arm.

4. The surgical device of claim 3, wherein the proximal flange of the second member slidably engages an inner surface of the cavity and provides stability during axial movement of the second member.

5. The surgical device of claim 1, wherein the first and second members are generally annular structures and the second member is concentrically attached to the first member.

6. The surgical device of claim 1 further comprising a needle attached to the distal end of the first member such that the needle is covered when the second member is in the second position.

7. The surgical device of claim 1, wherein the second member is movable between the second position and a third position, thereby providing indication that the second member is inhibited from moving from the second position to the first position.

8. The surgical device of claim 7, wherein the third position of the second member defines a gap between the distal end of the at least one arm and a surface of the proximal flange.

9. The surgical device of claim 7, further comprising a flange disposed at a distal end of the lock, the flange engaging a portion of the second member when the second member is in the third position.

10. The surgical device of claim 1, wherein the at least one arm moves toward the post when the second member is at an intermediate position between the first and second positions, further axial movement of the second member from the intermediate position to the second position causes the at least one arm to move away from the post.

11. The surgical device of claim 1, wherein said at least one arm comprises a first locking arm, the lock comprises a second locking arm spaced axially away from the first locking arm for securing the lock to the post.

12. A surgical device comprising:
a first member;
a second member slidably attached to the first member, the second member positionable amongst a plurality of positions; and
a lock disposed in the first member, the lock including at least one arm that is pivotably attached thereto, the at least one arm being biased radially outwards from an outer surface of the lock, wherein when the second member is in a first position, the second member is axially movable with respect to the first member and when the second member is in a second position, relative axial movement between the first and second members is inhibited by a distal end of the at least one arm contacting a surface of a flange disposed on the second member, axial movement of the second member from the first position to the second position moves the at least one arm radially inward toward the outer surface of the lock;
wherein an exterior surface of a distal end of the first member is exposed when the second member is in the first position such that direct contact with the distal end of the first member is permitted, and the exterior surface of the distal end of the first member is covered when the second member is in the second position such that the second member provides a barrier against direct contact with the distal end of the first member.

13. The surgical device of claim 12, wherein the second member is movable from the second position to a third position and the flange of the second member is spaced apart from the distal end of the at least one arm defining a gap therebetween.

14. The surgical device of claim 13, wherein movement of the second member between the second and third positions provides tactile feedback.

15. The surgical device of claim 13, wherein a distal portion of the lock engages a proximal portion of the second member when the second member is moved to the third position.

16. The surgical device of claim 12 further comprising a ring disposed on a proximal portion of the second member, the ring being slidably disposed in the cavity and provides stability to the second member.

17. The surgical device of claim 12 further comprising an actuator located on the second member and a portion of the actuator is positioned in a slot of the first member for guiding movement of the second member.

* * * * *